United States Patent [19]

Flemer, III

[11] Patent Number: Plant 7,147

[45] Date of Patent: Feb. 13, 1990

[54] *MALUS HUPEHENSIS* NAMED 'CARDINAL'

[75] Inventor: William Flemer, III, Princeton, N.J.

[73] Assignee: New Plant Associates, Princeton, N.J.

[21] Appl. No.: 292,114

[22] Filed: Dec. 30, 1988

[51] Int. Cl.[4] ..... A01H 5/00

[52] U.S. Cl. ..... Plt./34

[58] Field of Search ..... Plt./34

[56] References Cited

PUBLICATIONS den Boer, A. F., "Tea Crab", *Ornamental Crab Apples,* pub. The American Association of Nurseryman, Jul. 1959, pp. 164, 165.

*Primary Examiner*—James R. Feyrer

*Attorney, Agent, or Firm*—Frank B. Robb

[57] ABSTRACT

A *Malus hupehensis* tree providing abundant red flowers and small, very glossy red fruits, having resistance to defoliation in hot humid summers and to leaf injury from apple scab fungus or mildew which severely affects other similar trees in an adjacent area, the tree growing rapidly and displaying a wide spreading crown.

2 Drawing Sheets

DESCRIPTION OF THE INVENTION

This invention relates to a new variety of *Malus hupehensis* tree, commonly referred to as the flowering tea crab.

My new *Malus hupehensis* is one of a large number of ornamental trees which I have developed during many years of effort, and of which the flowering crab is a well known example.

The colorful tree of my new variety is one particularly selected from a row of seedlings of *Malus hupehensis* 'Strawberry Parfait', U.S. Plant Pat. No. 4,632×Malus 'Crimson Cloud' an unpatented variety of my development.

My new tree is comparable in height and spread to Malus 'Strawberry Parfait' but it is more densely branched. The branch crotch angles are wide, approximately 90 degrees on the average. The tree is lower growing and more spreading than *Crimson Cloud' and less densely branched than that variety. It is more flat topped than 'Crimson Cloud' which forms a large rounded crown.*

It may be noted that Malus 'Crimson Cloud' is a hybrid between *Malus baccata* and Malus 'Almey', neither patented, the latter itself a hybrid crab apple.

My new variety might desirably be called a hybrid crab apple, but it resembles *Malus hupehensis* in two important respects, it has the same spreading habit of growth with a flat top and it has the same extremely high resistance to apple scab disease and mildew. This aspect was particularly striking during the spring and summer of 1988 when almost all crab apples defoliated badly with the exception of *Malus hupehensis* and its hybrid progeny. The botanical name by which I have chosen to designate 'Cardinal' may be thought to be arbitrary, but its performance is the best of the red flowered crab apples in any event.

I point out that the blooms of my new variety are slightly larger, about 4.5 cm in diameter when fully expanded, than 'Strawberry Parfait', which is about 4.2 cm in diameter, and slightly smaller than 'Crimson Cloud' which may be 4.7 to 4.8 cm in diameter.

My new variety 'Cardinal' bears four to five fruits per spur in contrast to Malus 'Strawberry Parfait' which bears five to six fruits per spur and Malus 'Crimson Cloud' which bears three to four fruits per spur.

To define the distinctions between the several varieties herein referred to, it is noted that the fruit crop of Malus 'Strawberry Parfait' is abundant and showy. The color is vivid red 5R 5/13. 'Cardinal' is a less showy and abundant fruiter and the color is deeper, strong red 5R 4/12.

The fruit size of 'Cardinal' is larger than 'Strawberry Parfait' about 1 cm deep and 1.5 cm wide. 'Strawberry Parfait' is about 1 cm deep and 1 cm wide. The wild type of *Malus hupehensis* bears abundant but not conspicuous fruits.

Having been selected by me, I noted that as the tree matures it becomes more outstanding for its abundant bright red flowers and small, very glossy red fruits.

I have been able to select new varieties of *Malus hupehensis* because of the fact that, in the nursery to which I have access near Princeton, N.J., there are large numbers of such trees growing as well as many other ornamental trees of different species. The fact is that there many other ornamental trees also grown in the nursery and I am particularly watchful for the occurrence of new varieties of all kinds which provide desirable display and growth characteristics.

As a result of the observations conducted, I note that those previously mentioned aspects have been displayed even in very humid summers in New Jersey, during which my new variety here being described, did not exhibit defoliation or leaf injury from apple scab fungus, even though sibling seedlings showed severe defoliation.

In addition, an important commercial aspect of my new variety, is the rapid growth rate and the wide spreading crown.

I have established that the foregoing generally described characteristics and those specifically enumerated, continue from generation to generation created by asexual reproduction effected by bud grafting carried on near Plainsboro, N.J.

Further details of my new variety, which I have chosen to identify for commercial purposes as 'Cardinal', are set forth in the following detailed summary, as shown in the drawing wherein a tree of the new variety is shown in color as nearly representative of the actual tree, as it is possible to provide by photographic process.

The second sheet of drawings shows a portion of a branch of my new variety in larger detail.

The color notations are selected from the Nickerson Color Fan of Munsell Color Company and reflect the observations made in ordinary daylight conditions.

DETAILED DESCRIPTION OF THE INVENTION

Parentage:

*Seed parent.*—*Malus hupehensis* 'Strawberry Parfait' U.S. Plant Pat. No. 4,632.

*Pollen parent.*—Malus 'Crimson Cloud ' (unpatented).

Tree: Medium height, about 5.18 meters, widespreading; commonly to a width of 9.75 meters; dense and hardy.

*Trunk.*—Stocky and smooth. Diameter 12.18 cm.

*Branches.*—Slender and smooth; begin about 1.32 meters above ground. Color — Dark grayish purple. Lenticels — Sparse; number — 4 to 5 per cm of twig.

*Bark.*—Smooth and brownish gray 10YR 3/1 in color.

Leaves:

*Quantity.*—Moderately abundant.

*Length.*—8 to 9 cm.

*Width.*—3 to 3.5 cm.

*Shape.*—Narrow ovate.

*Color.*—When expanding — Moderate reddish brown, 7.5R 3/6. Summer — Dark red 2.5R 3/1.

*Thick.*—Not susceptible to apple scab fungus or mildew.

*Stipules.*—2 cm long — drop when foliage and twigs mature.

*Margin.*—Serrate.

*Petiole.*—Medium 3 to 4 cm long.

*Glands.*—None.

Flower buds:

*Hardiness.*—Very cold hardy.

*Size.*—0.5 cm long, 0.2 cm wide.

*Shape.*—Minute, ovate.

*Color.*—Dark purple.

Flowers:

*Dates first bloom.*—April 27.

*Full bloom.*—May 4. Considered mid-season regular bloomer in New Jersey, about the same time as Malus 'Strawberry Parfait' and seven to ten days later than 'Crimson Cloud'.

*Quantity.*—Very abundant.

*Size.*—Large. 4.5 cm diameter when fully expanded.

*Color.*—Strong red 5R4/10, fading to moderate red 2.5R 4/10 when fully opened.

Petalage:

*Number of petals.*—5.

*Shape of petals.*—Rounded, slightly notched at end.

*Size of petals.*—Length 2 cm, width 1.6 cm.

*Color.*—Moderate red, 2.5R 4/10.

Fruits:

*When borne.*—September, October.

*Abundance.*—Moderately abundant, glossy.

*Seed cells.*—Average two to five per fruit; mature seeds moderate reddish brown 2.5YR 3/3.

*Size.*—1 cm deep, 1.5 cm wide.

*Color.*—Strong red 5R 4/12.

I claim:

1. A new and distinct variety of *Malus hupehensis* tree substantially as herein shown and described, characterized particularly as to novelty, by the abundant bright red flowers and small, very glossy red fruits produced, the ability to resist defoliation and leaf injury from apple scab fungus or mildew under conditions severely affecting other trees of *Malus hupehensis* growing in the same area, and the rapid growth rate of the new variety, with wide spreading crown.

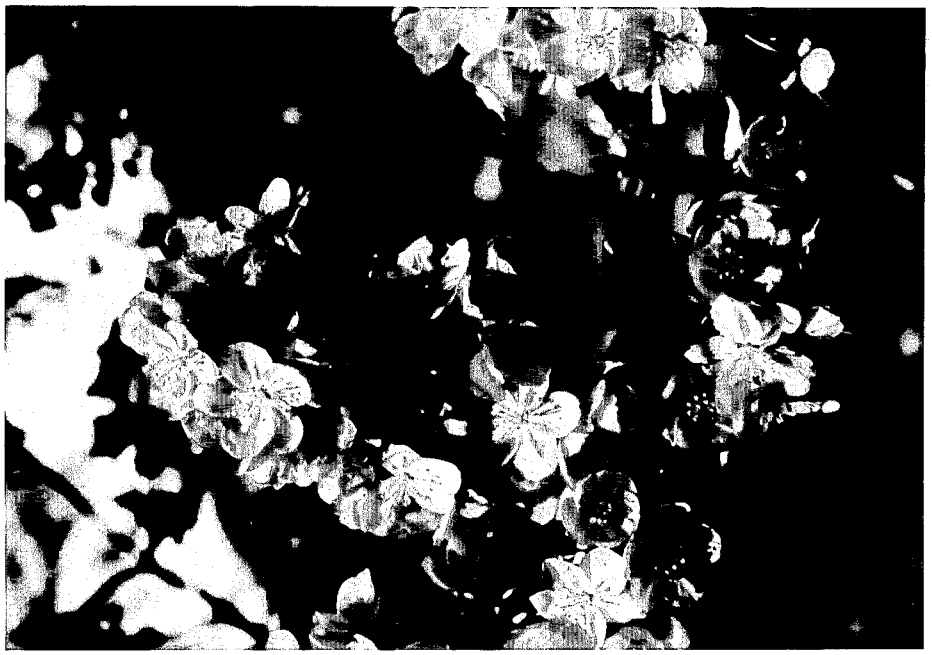

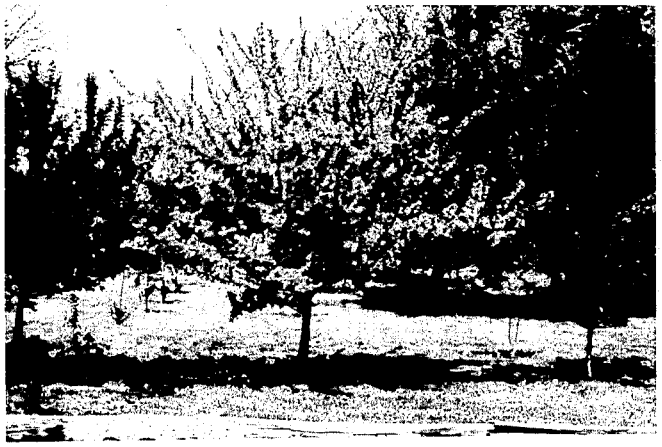

* * * * *